United States Patent
Schotes

(10) Patent No.: US 10,633,321 B2
(45) Date of Patent: Apr. 28, 2020

(54) METHOD FOR PRODUCING CYCLOPROPYL-SUBSTITUTED ACETOPHENONES

(71) Applicant: Bayer CropScience Aktiengesellschaft, Monheim am Rhein (DE)

(72) Inventor: Christoph Schotes, Düsseldorf (DE)

(73) Assignee: Bayer CropScience Aktiengesellschaft, Monheim Am Rhein (DE)

( * ) Notice: Subject to any disclaimer, the term of this patent is extended or adjusted under 35 U.S.C. 154(b) by 0 days.

(21) Appl. No.: 16/337,798

(22) PCT Filed: Sep. 29, 2017

(86) PCT No.: PCT/EP2017/074802
§ 371 (c)(1),
(2) Date: Mar. 28, 2019

(87) PCT Pub. No.: WO2018/065316
PCT Pub. Date: Apr. 12, 2018

(65) Prior Publication Data
US 2020/0002259 A1 Jan. 2, 2020

(30) Foreign Application Priority Data
Oct. 5, 2016 (EP) .................... 16192300

(51) Int. Cl.
*C07C 45/58* (2006.01)
*C07C 49/225* (2006.01)

(52) U.S. Cl.
CPC ............ *C07C 49/225* (2013.01); *C07C 45/58* (2013.01)

(58) Field of Classification Search
CPC .............................. C07C 45/58; C07C 49/225
See application file for complete search history.

(56) References Cited

FOREIGN PATENT DOCUMENTS

| CN | 101857576 | 10/2010 |
| CN | 102603508 | 3/2014 |

OTHER PUBLICATIONS

Arroyo et al. Stereoselective Alkylidenation of Ketones with 2-(p-Toluenesulinyl) benzyl Iodide: Synthesis of Enantiomerically Pure Trisubstituted Epoxides. Organic Letters. vol. 10 (11), 2151-2154. (Year: 2008).*
International Search Report dated Dec. 22, 2017, for PCT/EP2017/074802, filed Sep. 29, 2017, 2 pages.

* cited by examiner

*Primary Examiner* — Sikarl A Witherspoon
(74) *Attorney, Agent, or Firm* — Morrison & Foerster, LLP

(57) ABSTRACT

A method is described for preparing cyclopropyl-substituted acetophenones of the general formula (I).

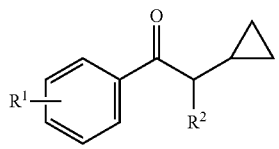

(I)

10 Claims, No Drawings

METHOD FOR PRODUCING CYCLOPROPYL-SUBSTITUTED ACETOPHENONES

CROSS REFERENCE TO RELATED APPLICATIONS

This application is a national stage application under 35 U.S.C. § 371 of International Application No. PCT/EP2017/074802, filed internationally on Sep. 29, 2017, which claims the benefit of European Application No. 16192300.8, filed Oct. 5, 2016.

The invention relates to a method for preparing cyclopropyl-substituted acetophenones and also to two compounds which are used in the method.

Cyclopropyl-substituted acetophenones are important intermediates for the synthesis of agrochemically active substances such as cyproconazole and have already been prepared by diverse routes. Examples include here two syntheses related to the method according to the invention:

CN 101857576A (2010) discloses a method in which the cyclopropyl-substituted acetophenone 1-(4-chlorophenyl)-2-cyclopropylpropan-1-one is prepared by adding 4-chlorobenzylmagnesium chloride to cyclopropyl methyl ketone, followed by eliminating the resulting hydroxyl group, hydroboration and oxidation initially to the benzylic alcohol, then further to give 1-(4-chlorophenyl)-2-cyclopropylpropan-1-one. A disadvantage of this method is the hydroboration reaction, which is safety-critical and is also expensive.

CN102603508B likewise describes the preparation of 1-(4-chlorophenyl)-2-cyclopropylpropan-1-one but starting from methyl 2-chloro-2-(4-chlorophenyl)acetate. This is reacted with a strong base and methyl cyclopropyl ketone to give a glycidyl ester, which rearranges after saponification and acidification to give 1-(4-chlorophenyl)-2-cyclopropylpropan-1-one. A disadvantage here is the use of methyl 2-chloro-2-(4-chlorophenyl)acetate as starting material, which firstly has to be prepared in a multi-stage synthesis and which therefore increases the costs of the method.

The object of the present invention is to provide a method for preparing cyclopropyl-substituted acetophenones which overcomes the disadvantages of the methods known from the prior art.

This object is achieved by a method for preparing cyclopropyl-substituted acetophenones (I),

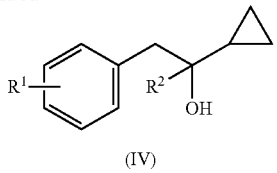

(I)

in which
a) in a first step a benzylmagnesium halide or benzylzinc halide (II) is reacted with a cyclopropyl alkyl ketone (III) to give an alcohol (IV),

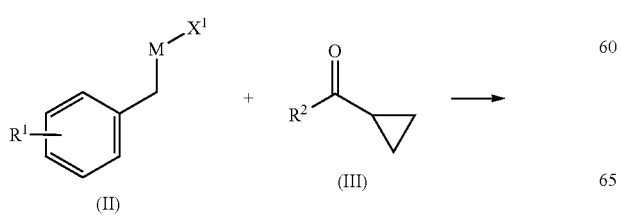

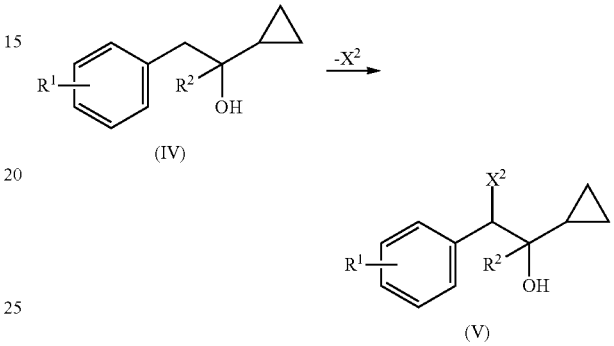

b) in a second step the alcohol (IV) is converted to a halohydrin (V) by free-radical halogenation,

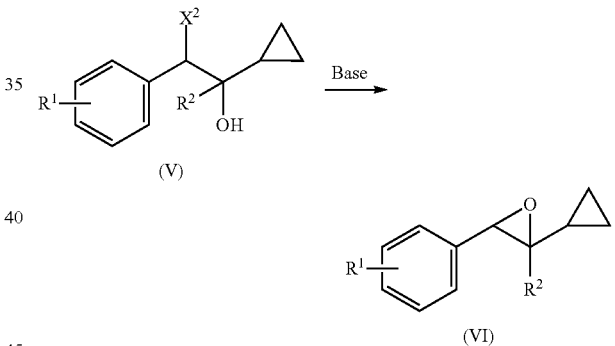

c) in a third step the halohydrin (V) is converted to an epoxide (VI) by addition of base,

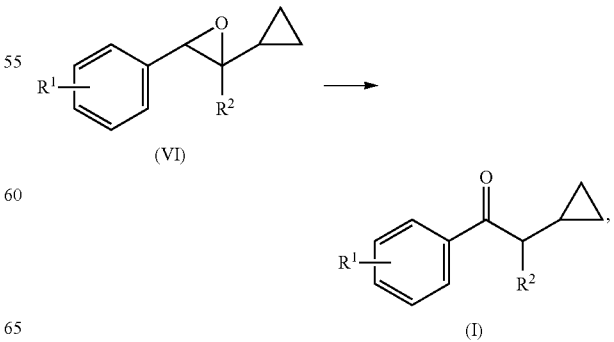

d) in a fourth step the epoxide (VI) is converted to the cyclopropyl-substituted acetophenone (I) under thermal Lewis acid or Brønsted acid conditions where $R^1$ is chlorine, bromine, iodine, alkoxy, amino, cyano, nitro, $C_1$-$C_4$-alkyl or is unsubstituted phenyl or phenyl substituted by s radicals selected from the group consisting of chlorine, fluorine, methoxy and ethoxy, $R^2$ is $C_1$-$C_4$-alkyl or is unsubstituted phenyl or phenyl substituted by s radicals selected from the group consisting of chlorine, fluorine, methoxy and ethoxy, s is 1, 2 or 3, M is magnesium or zinc, $X^1$, $X^2$ are each independently chlorine, bromine or iodine.

According to a preferred embodiment, $X^1$ may be chlorine.

It is also preferred if $X^2$ is bromine.
It is also preferred if $R^1$ is 4-chlorine.
It is also preferred if M is magnesium.
It is also preferred if $R^2$ is methyl.
It is especially preferred if $X^1$ is chlorine, $X^2$ is bromine, $R^1$ is 4-chlorine, M is magnesium and $R^2$ is methyl.

In the formulae (I), (II), (III), (IV), (V) and (VI), alkyl radicals having more than two carbon atoms may be straight-chain or branched. Suitable alkyl radicals are e.g. methyl, ethyl, n- or isopropyl, n-, iso, t- or 2-butyl.

Compound (II) may be prepared by reacting a benzyl halide with magnesium to give the corresponding benzylmagnesium halide, wherein a ratio of magnesium to benzyl halide of from 0.9:1 to 20:1 may be used.

In the first step of the method according to the invention, the benzylmagnesium halide of the formula (II) is reacted with a cyclopropyl alkyl ketone (III) to give an alcohol (IV).

The reaction is generally carried out in a solvent. Suitable solvents are aliphatic and aromatic hydrocarbons such as n-hexane, benzene or toluene and ethers such as diphenyl ether, methyl tert-butyl ether, isopropyl ethyl ether, dioxane, diglyme, dimethyl glycol and THF and mixtures of such solvents. Preference is given to toluene/THF mixtures and diethyl ether. Particular preference is given to diethyl ether.

The reaction can be carried out in a temperature range of from −40 to 200° C. Preference is given to −20 to 50° C., particular preference to 0 to 40° C. The reaction is generally conducted at standard pressure but can also be conducted at elevated or reduced pressure.

In the second step of the method according to the invention, the alcohol (IV) is converted to a halohydrin (V) by free-radical halogenation.

The halogen radical used for the halogenation may be generated from a halogenating reagent by exposure to heat or radiation (UV or visible light) and optionally a radical initiator.

Suitable halogenating reagents are, for example, the following substances: N-chlorosuccinimide, N-bromosuccinimide, N-iodosuccinimide, chlorine, bromine, iodine, bromotrichloromethane, 1,3-dichloro-5,5-dimethylhydantoin, 1,3-dibromo-5,5-dimethylhydantoin and sulphuryl chloride. Preference is given to N-bromosuccinimide. The ratio of the compound of the formula (IV) to the halogenating reagent is preferably between 1:0.9 and 1:10.

Particularly suitable as radical initiators are dibenzoyl peroxide, 2,2'-azobis(2-methylpropionitrile) (AIBN) and di-tert-butyl peroxide, which may be used in an amount of 0.1 to 50 mole percent based on the compound of the general formula (IV). Preference is given to using 1 to 20 mole percent of the radical initiator.

The reaction temperature in the second step of the method according to the invention can be between 0 and 150° C. Preference is given to 20 to 90° C., particular preference to 60 to 80° C.

The reaction is generally conducted at standard pressure but can also be conducted at elevated or reduced pressure.

It is possible in principle to use as diluent in this step all organic solvents inert under the reaction conditions. Examples include: ethers such as methyl tert-butyl ether, methyl cyclopentyl ether, 2-methyltetrahydrofuran, 1,4-dioxane; hydrocarbons such as cyclohexane, methylcyclohexane, toluene, xylenes, mesitylene, chlorobenzene, 1,2-dichlorobenzene, dichloromethane, tetrachloromethane, chloroform; nitriles such as acetonitrile, butyronitrile; amides such as N,N-dimethylformamide, N,N-dimethylacetamide, N-methylpyrrolidone; dimethyl sulphoxide or sulpholane.

In the third step of the method according to the invention, the halohydrin (V) is converted to an epoxide (VI) by addition of base.

The reaction can be carried out in the presence of inorganic bases such as LiOH, NaOH, KOH, Ca(OH)$_2$, Na$_2$CO$_3$, K$_2$CO$_3$, Cs$_2$CO$_3$, NaOMe, NaOEt, NaO-t-Bu, KO-t-Bu or organic bases such as trialkylamines, alkylpyridines, phosphazenes and 1,8-diazabicyclo[5.4.0]undecene (DBU). Preference is given to NaOH and KOtBu, particular preference being given to KO-t-Bu.

The bases may be used in a ratio of from 1:0.9 to 1:20, based on compound (V).

If the bases are used as aqueous solutions, a phase transfer catalyst is additionally added such as, for example, ammonium or phosphonium salts such as tetrahexylammonium chloride, tetrahexylammonium bromide, tetrahexylammonium iodide, tetraoctylammonium chloride, tetraoctylammonium bromide, tetraoctylammonium iodide, Aliquat HTA-1®, Aliquat 134®, dimethyldidecylammonium chloride, dimethyldodecylbenzylammonium chloride, tributylhexadecylammonium chloride, tributylhexadecylammonium bromide, tributyltetradecylphosphonium chloride and tributyltetradecylphosphonium bromide. Preference is given to Aliquat 134®.

The phase transfer catalyst is typically used in an amount of from 0.1 to 50 mole percent, based on the compound (V). Preference is given to 5 to 20 mole percent.

It is possible in principle to use as diluent in this reaction all organic solvents inert under the reaction conditions. Examples include: ethers such as methyl tert-butyl ether, diethyl ether, tetrahydrofuran, methyl cyclopentyl ether, 2-methyltetrahydrofuran, 1,4-dioxane; hydrocarbons such as cyclohexane, methylcyclohexane, toluene, xylenes, mesitylene, chlorobenzene, 1,2-dichlorobenzene, dichloromethane; nitriles such as acetonitrile, butyronitrile; amides such as N,N-dimethylformamide, N,N-dimethylacetamide, N-methylpyrrolidone; dimethyl sulphoxide or sulpholane. Preference is given to THF, toluene and chlorobenzene.

The reaction in the third step of the method according to the invention is generally carried out at a temperature of −20 to 70° C., preferably 0 to 20° C. The reaction is generally conducted at standard pressure, but can also be conducted at elevated or reduced pressure.

In the fourth step of the method according to the invention the epoxide (VI) is converted to the cyclopropyl-substituted acetophenone (I) under thermal Lewis acid or Brønsted acid conditions.

Lewis acids include, for example: boron trifluoride, aluminium trichloride, zinc triflate, scandium triflate, zinc chloride, zinc bromide, copper(II) chloride, titanium tetrachloride, trimethylsilyl chloride, tin tetrachloride, cerium trichloride, magnesium chloride, iron dichloride and iron trichloride. Particularly suitable are cerium trichloride, zinc triflate, zinc chloride and scandium triflate.

Suitable Brønsted acids are mineral acids such as $H_2SO_4$, HCl, $HSO_3Cl$, HF, HBr, HI, $H_3PO_4$ or organic acids such as $CF_3COOH$, p-toluenesulphonic acid, methanesulphonic acid, camphorsulphonic acid or trifluoromethanesulphonic acid. Particularly suitable are camphorsulphonic acid and methanesulphonic acid.

The Brønsted and Lewis acids may be added in a proportion of 0.1 to 50 mol %, based on compound (VI). Preference is given to 5 to 30 mol %, particular preference being given to 10 to 20 mol %.

The reaction in the fourth step of the method according to the invention is generally carried out in a solvent.

Suitable solvents are aliphatic and aromatic hydrocarbons such as n-hexane, benzene or toluene, which may be substituted by heteroatoms such as fluorine or chlorine, such as dichloromethane, dichloroethane, chlorobenzene or dichlorobenzene. Likewise suitable are ethers such as diphenyl ether, methyl tert-butyl ether, isopropyl ethyl ether, dioxane, diglyme, dimethyl glycol, and THF and mixtures of such solvents. Preference is given to methyl tert-butyl ether, toluene and chlorobenzene. Particular preference is given to toluene and chlorobenzene.

The reaction temperature is between 0 and 100° C., preferably 20 to 80° C. The reaction is generally conducted at standard pressure but can also be conducted at elevated or reduced pressure.

The invention likewise provides a compound of the general formula (V),

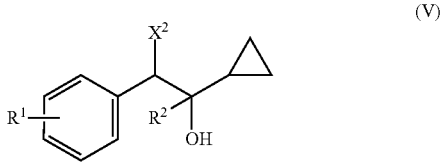

(V)

where
$R^1$ is chlorine, bromine, iodine, alkoxy, amino, cyano, nitro, $C_1$-$C_4$-alkyl or is unsubstituted phenyl or phenyl substituted by s radicals selected from the group consisting of chlorine, fluorine, methoxy and ethoxy,
$R^2$ is $C_1$-$C_4$-alkyl or is unsubstituted phenyl or phenyl substituted by s radicals selected from the group consisting of chlorine, fluorine, methoxy and ethoxy,
s is 1, 2 or 3,
$X^2$ is chlorine, bromine or iodine.

According to a preferred embodiment of the compounds of the formula (V), $X^2$ may be bromine.

It is preferred if $R^1$ is 4-chlorine.
It is also preferred if $R^2$ is methyl.
It is especially preferred if $X^2$ is bromine, $R^1$ is 4-chlorine and $R^2$ is methyl.

The invention likewise provides a compound of the general formula (VI),

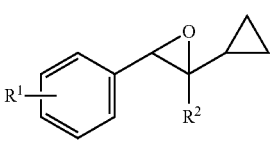

(VI)

where
$R^1$ is chlorine, bromine, iodine, alkoxy, amino, cyano, nitro, $C_1$-$C_4$-alkyl or is unsubstituted phenyl or phenyl substituted by s radicals selected from the group consisting of chlorine, fluorine, methoxy and ethoxy,
$R^2$ is $C_1$-$C_4$-alkyl or is unsubstituted phenyl or phenyl substituted by s radicals selected from the group consisting of chlorine, fluorine, methoxy and ethoxy,
s is 1, 2 or 3.

According to a preferred embodiment of the compounds of the formula (VI), $R^1$ may be 4-chlorine.

It is likewise preferred if $R^2$ is methyl.
It is especially preferred if $R^1$ is 4-chlorine and $R^2$ is methyl.

The examples which follow elucidate more particularly the invention.

Preparation of
1-(4-chlorophenyl)-2-cyclopropylpropan-1-one

Step 1:
1-(4-chlorophenyl)-2-cyclopropylpropan-2-ol

Magnesium turnings (30.4 g, 1.25 mol, 2 equiv) were charged in 300 ml of diethyl ether with a trace of iodine. 4-Chlorobenzyl chloride (100.6 g, 625 mmol, 1 equiv) was dissolved in 200 ml of diethyl ether and added dropwise to the magnesium. After the end of the addition, the reaction mixture was maintained at reflux for 10 min. The reaction mixture was cooled to 0° C. and cyclopropyl methyl ketone in 100 ml of diethyl ether was added dropwise such that the internal temperature did not exceed 10° C. Subsequently, the reaction mixture was stirred at room temperature for a further 2 h. The reaction mixture was quenched with 80 ml of saturated ammonium chloride solution and 50 ml of water were added. The resulting suspension was filtered off through kieselguhr and rinsed with methyl tert-butyl ether. The organic phase was separated and washed with water and brine and then dried over sodium sulphate, filtered and concentrated by rotary evaporation. This gave 122 g of 1-(4-chlorophenyl)-2-cyclopropylpropan-2-ol at a purity of 100% (GCa/a) (85% yield).

$^1$H NMR (602 MHz, DMSO-$d_6$) δ=7.32-7.23 (m, 4H), 3.98 (s, 1H), 2.72-2.65 (m, 2H), 0.96 (s, 3H), 0.76 (tt, J=5.4, 8.4 Hz, 1H), 0.34-0.23 (m, 2H), 0.21-0.15 (m, 2H). GC/MS: m/e=192 (M-$H_2O$).

Step 2: 1-bromo-1-(4-chlorophenyl)-2-cyclopropyl-propan-2-ol 1-(4-chlorophenyl)-2-cyclopropylpropan-2-ol (20 g, 87.1 mmol, 1 equiv) was stirred in chlorobenzene (200 ml) together with N-bromosuccinimide (26.54 g, 148 mmol, 1.7 equiv) and 2,2'-azobis(2-methylpropionitrile) (0.85 g, 3.5 mmol, 0.04 equiv) at 70° C. for 44 h. The reaction mixture was filtered through silica gel and washed through with chlorobenzene. After removal of the solvent, 27.6 g (59% yield, purity 79.3% a/a HPLC) of a crude product resulted, which was purified by column chromatography (silica gel, cyclohexane/ethyl acetate gradient 0-20% v/v) to a purity of 96.6% a/a by HPLC.

Diastereoisomer A: $^1$H NMR (602 MHz, DMSO-$d_6$) δ=7.56-7.50 (m, 2H), 7.41-7.36 (m, 2H), 5.21 (s, 1H), 4.70 (s, 1H), 1.27 (s, 1H), 0.87 (tt, J=-5.4, 8.4 Hz, 1H), 0.51-0.43 (m, 1H), 0.32-0.13 (m, 2H), 0.08-0.02 (m, 1H). Diastereoisomer B: $^1$H NMR (602 MHz, DMSO-$d_6$) δ=7.56-7.50 (m, 2H), 7.36-7.32 (m, 2H), 5.16 (s, 1H), 4.65 (s, 1H), 1.12 (s, 3H), 0.79-0.73 (m, 1H), 0.32-0.13 (m, 3H), −0.04-0.10 (m, 1H). GC/MS: m/e=208 (M-HBr).

Step 3:
3-(4-chlorophenyl)-2-cyclopropyl-2-methyloxirane 1-bromo-1-(4-chlorophenyl)-2-cyclopropylpropan-2-ol (5 g, 15.7 mmol, 1 equiv) was charged in 50 ml of toluene and cooled to 0° C. Potassium tert-butoxide (2.7 g, 23.6 mmol, 1.5 equiv) was then added. The reaction mixture was allowed to warm to room temperature and then stirred at this temperature for 2.5 hours. The reaction mixture was filtered through kieselguhr and used directly for the 4th step.

Diastereoisomer A: $^1$H NMR (602 MHz, DMSO-$d_6$) δ=7.44-7.39 (m, 2H), 7.38-7.34 (m, 2H), 3.99 (s, 1H), 1.22 (tt, J=5.2, 8.3 Hz, 1H), 0.56-0.22 (m, 4H). Diastereoisomer B: $^1$H NMR (602 MHz, DMSO-d) δ=7.44-7.39 (m, 2H), 7.31-7.27 (m, 2H), 3.87 (s, 1H), 1.01 (s, 3H), 0.54-0.23 (m, 5H). GC/MS: m/e=208 (M).

Step 4:
1-(4-chlorophenyl)-2-cyclopropylpropan-1-one

Zinc chloride (0.43 g, 3.16 mmol, 0.2 equiv) was added to the toluene solution from step 3 and the mixture stirred at room temperature for 15 h. The resulting suspension was filtered through silica gel and the solvent was removed under reduced pressure. This gave 3.9 g of 1-(4-chlorophenyl)-2-cyclopropylpropan-1-one as crude product which was purified by column chromatography (silica gel, cyclohexane/ethyl acetate gradient 0-20% v/v) to a purity of 94% a/a (HPLC a/a) (2.02 g 55% yield over 2 steps).

$^1$H NMR (602 MHz, DMSO-$d_6$) δ=7.98-7.94 (m, 2H), 7.60-7.57 (m, 2H), 2.96 (qd, J=6.9, 9.1 Hz, 1H), 1.15 (d, J=6.9 Hz, 3H), 0.93-0.85 (m, 1H), 0.48 (ddt, J=3.9, 5.3, 8.7 Hz, 1H), 0.40-0.33 (m, 1H), 0.26-0.13 (m, 2H). GC/MS: m/e=208 (M).

The invention claimed is:
1. A method for preparing a cyclopropyl-substituted acetophenone of formula (I),

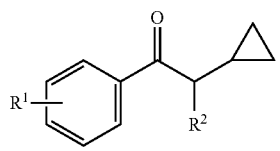

(I)

comprising
a) in a first step reacting a benzylmagnesium halide or a benzylzinc halide (II) with a cyclopropyl alkyl ketone (III) to give an alcohol (IV),

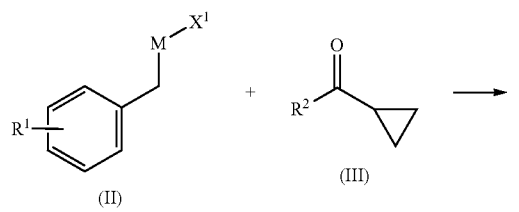

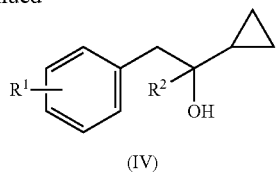

(IV)

b) in a second step converting the alcohol (IV) to a halohydrin (V) by free-radical halogenation,

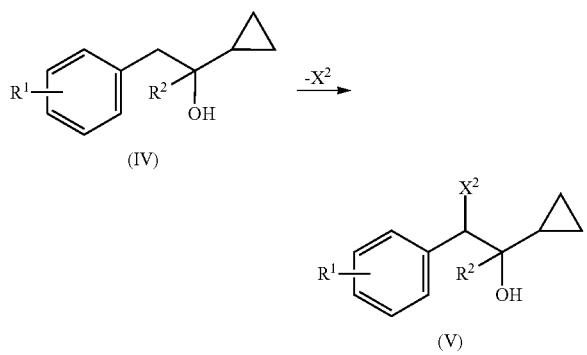

c) in a third step converting the halohydrin (V) to an epoxide (VI) by addition of base,

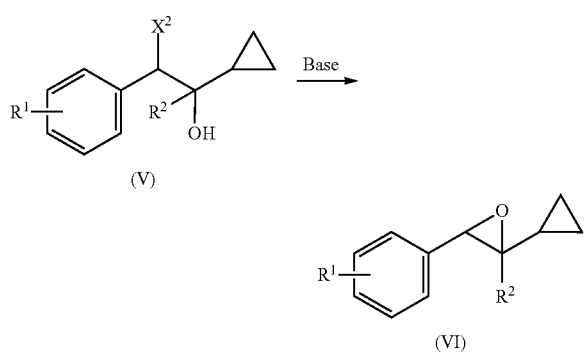

d) in a fourth step converting the epoxide (VI) to the cyclopropyl-substituted acetophenone (I) under thermal Lewis acid or Brønsted acid conditions,

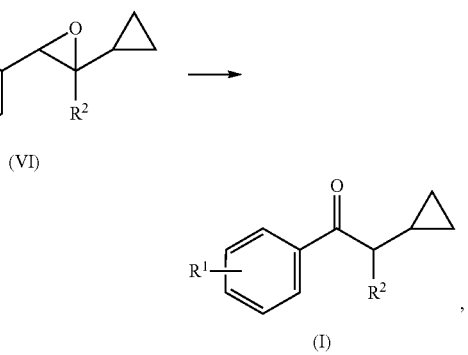

, wherein

R¹ is chlorine, bromine, iodine, alkoxy, amino, cyano, nitro, $C_1$-$C_4$-alkyl or is unsubstituted phenyl or phenyl substituted by s radicals selected from the group consisting of chlorine, fluorine, methoxy and ethoxy, R² is $C_1$-$C_4$-alkyl or is unsubstituted phenyl or phenyl substituted by s radicals selected from the group consisting of chlorine, fluorine, methoxy and ethoxy, s is 1, 2 or 3, X¹, X² are each independently chlorine, bromine or iodine.

2. The method according to claim 1, wherein X¹ is chlorine.

3. The method according to claim 1, wherein X² is bromine.

4. The method according to claim 1, wherein R¹ is 4-chlorine.

5. The method according to claim 1, wherein R² is methyl.

6. The method according to claim 1, wherein X¹ is chlorine, X² is bromine, R¹ is 4-chlorine and R² is methyl.

7. A compound of formula (V),

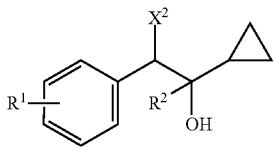

(V)

wherein

R¹ is chlorine, bromine, iodine, alkoxy, amino, cyano, nitro, $C_1$-$C_4$-alkyl or is unsubstituted phenyl or phenyl substituted by s radicals selected from the group consisting of chlorine, fluorine, methoxy and ethoxy, R² is $C_1$-$C_4$-alkyl or is unsubstituted phenyl or phenyl substituted by s radicals selected from the group consisting of chlorine, fluorine, methoxy and ethoxy, s is 1, 2 or 3, X² is chlorine, bromine or iodine.

8. The compound according to claim 7, wherein X² is bromine, R¹ is 4-chlorine and R² is methyl.

9. A compound of formula (VI),

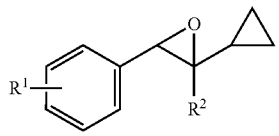

(VI)

wherein

R¹ is chlorine, bromine, iodine, alkoxy, amino, cyano, nitro, $C_1$-$C_4$-alkyl or is unsubstituted phenyl or phenyl substituted by s radicals selected from the group consisting of chlorine, fluorine, methoxy and ethoxy, R² is $C_1$-$C_4$-alkyl or is unsubstituted phenyl or phenyl substituted by s radicals selected from the group consisting of chlorine, fluorine, methoxy and ethoxy, s is 1, 2 or 3.

10. The compound according to claim 9, wherein R¹ is 4-chlorine and R² is methyl.

* * * * *